(12) United States Patent
Kim

(10) Patent No.: US 12,061,171 B2
(45) Date of Patent: Aug. 13, 2024

(54) METHOD FOR ANALYZING DAMPING CHARACTERISTICS OF CARBON COMPOSITE MATERIAL USING VISCOUS DAMPING COEFFICIENT OF CARBON FIBER AND SYSTEM FOR ANALYZING DAMPING CHARACTERISTICS OF CARBON COMPOSITE MATERIAL USING SAME

(71) Applicant: PUKYONG NATIONAL UNIVERSITY INDUSTRY-UNIVERSITY COOPERATION FOUNDATION, Busan (KR)

(72) Inventor: Chan-Jung Kim, Busan (KR)

(73) Assignee: Pukyong National University Industry-Univesity Cooperation Foundation, Busan (KR)

( * ) Notice: Subject to any disclaimer, the term of this patent is extended or adjusted under 35 U.S.C. 154(b) by 295 days.

(21) Appl. No.: 17/451,044

(22) Filed: Oct. 15, 2021

(65) Prior Publication Data

US 2023/0076617 A1 Mar. 9, 2023

(30) Foreign Application Priority Data

Sep. 9, 2021 (KR) .......................... 10-2021-0120284

(51) Int. Cl.
*G01N 29/04* (2006.01)
*G01N 29/44* (2006.01)
*G01N 33/00* (2006.01)

(52) U.S. Cl.
CPC ............ *G01N 29/045* (2013.01); *G01N 29/44* (2013.01); *G01N 33/00* (2013.01); *G01N 2033/0003* (2013.01); *G01N 2291/0231* (2013.01)

(58) Field of Classification Search
CPC ...... G01N 29/045; G01N 29/44; G01N 33/00; G01N 2033/0003; G01N 2291/0231; G01N 29/12; G01N 2291/014; Y02T 90/00

See application file for complete search history.

(56) References Cited

U.S. PATENT DOCUMENTS

2012/0313307 A1* 12/2012 Cartwright ............... C08J 5/042
267/141

FOREIGN PATENT DOCUMENTS

| KR | 10-2051746 B1 | 12/2019 | |
|---|---|---|---|
| KR | 10-2223538 B1 | 3/2021 | |
| TR | 202011808 A2 * | 8/2021 | ............... G01H 1/14 |

OTHER PUBLICATIONS

English machine translation of TR 202011808 A2 (Year: 2021).*

(Continued)

*Primary Examiner* — Roy Y Yi
*Assistant Examiner* — Geoffrey T Evans
(74) *Attorney, Agent, or Firm* — Knobbe, Martens, Olson & Bear, LLP

(57) ABSTRACT

This application relates to an apparatus and method for analyzing the damping characteristics of a carbon composite material. Damping analysis of carbon composite material using modal damping ratio is a conventional method that cannot accurately represent viscous damping coefficient variation but has errors in a sensitivity analysis. The damping characteristics of the carbon composite material were described by a parallel combination of the viscous damping coefficient of carbon fiber and binding matrix. The damping characteristics of the carbon composite material were expressed with the sensitivity index calculated only from the viscous damping coefficient of the carbon fiber by removing the viscous damping coefficient of the binding matrix that does not change depending on the carbon fiber direction.

(Continued)

Various embodiments improve accuracy in analyzing the damping characteristics of carbon composite material.

12 Claims, 10 Drawing Sheets

(56) References Cited

OTHER PUBLICATIONS

Kim, "Sensitivity of the Viscous Damping Coefficient of Carbon Fiber in Carbon-Fiber-Reinforced Plastic with Respect to the Fiber Angle", Crystals 2021, 11, 781.
Korean Patent Application No. 10-2021-0075856, filed Jun. 11, 2021, with English abstract.

* cited by examiner

FIG. 4

| Specimen | Resonance Frequency (Hz) | Modal Damping Coefficient (%) | Mode Shape |
|---|---|---|---|
| $\theta_0 = 0°$ | 1149.1 | 0.4 | Bending (first) |
| | 1276.1 | 2.5 | Twisting (first) |
| | 1368.7 | 1.3 | Twisting (second) |
| | 2990.9 | 1.3 | Bending (second) |
| | 951.0 | 5.3 | Bending (third) |
| $\theta_1 = 30°$ | 360.6 | 0.39 | Bending (first) |
| | 754.5 | 0.21 | Twisting (first) |
| | 941.1 | 0.82 | Twisting (second) |
| | 1657.6 | 0.01 | Bending (second) |
| | 1450.4 | 0.55 | Bending (third) |
| $\theta_2 = 45°$ | 330.4 | 1.3 | Bending (first) |
| | 595.6 | 1.4 | Twisting (first) |
| | 878.0 | 1.0 | Twisting (second) |
| | 1568.9 | 1.2 | Bending (second) |
| | 1749.2 | 1.5 | Bending (third) |
| $\theta_3 = 60°$ | 310.6 | 1.1 | Bending (first) |
| | 458.5 | 1.5 | Twisting (first) |
| | 979.0 | 1.3 | Twisting (second) |
| | 835.0 | 0.9 | Bending (second) |
| | 2690.4 | 3.9 | Bending (third) |
| $\theta_4 = 90°$ | 305.1 | 0.9 | Bending (first) |
| | 380.0 | 1.7 | Twisting (first) |
| | 1938.5 | 3.7 | Twisting (second) |
| | 824.1 | 0.9 | Bending (second) |
| | 3305.1 | 5.3 | Bending (third) |

METHOD FOR ANALYZING DAMPING CHARACTERISTICS OF CARBON COMPOSITE MATERIAL USING VISCOUS DAMPING COEFFICIENT OF CARBON FIBER AND SYSTEM FOR ANALYZING DAMPING CHARACTERISTICS OF CARBON COMPOSITE MATERIAL USING SAME

CROSS REFERENCE TO RELATED APPLICATION

The present application claims priority to Korean Patent Application No. 10-2021-0120284, filed Sep. 9, 2021, the entire contents of which is incorporated herein for all purposes by this reference.

BACKGROUND

Technical Field

The present disclosure relates to an apparatus and a method for analyzing the damping characteristics of a carbon composite material and, more specifically, to a method for analyzing the damping characteristics of a carbon composite material using a viscous damping coefficient of carbon fiber and a damping characteristics analysis system of a carbon composite material using the same.

Description of the Related Technology

In general, a carbon composite material is configured to have enhanced physical and chemical properties that may not be obtained as a single material by combining carbon fiber with various other materials as necessary.

In addition, recently, carbon composite material that is lighter and has higher strength than existing materials, such as carbon-fiber-reinforced plastic (CFRP), has been widely used in various fields such as automobiles and aerospace.

Here, since the physical properties of the carbon composite material such as CFRP are considerably changed according to the structure or the type of material due to the characteristics of being bonded with different materials, the carbon composite material with properties suitable for design purposes should be used. For this, it is essential to accurately understand the mechanical and physical properties of the carbon composite material, such as damping properties.

In other words, damping means that external load energy is converted into internal energy and offset by using the unique characteristics of each material. Thus, the damping characteristics of each material greatly influence the durability of the relevant material.

In addition, in order to physically exhibit and analyze these damping characteristics, conventionally, a damping coefficient, a modal damping ratio, and a sensitivity measured in a time domain or a frequency domain through a modal test have been generally used.

Here, as an example of the prior art for an apparatus and method for analyzing the physical properties of a specific material, such as the damping properties of the carbon composite material, for example, a "Sensitivity analysis device using frequency response and a sensitivity analysis method using the same", as presented in Korean Patent No. 10-2223538.

More specifically, Korean Patent No.10-2223538 relates to a sensitivity analysis apparatus using frequency response and a sensitivity analysis method using the same. The above-mentioned patent discloses including an exciter for setting an excitation pattern by control, and applying a physical force to one side of a test object according to the set excitation pattern; a first sensor contacting one side of the test object and measuring a physical force applied to the test object by the exciter; a second sensor contacting the other side of the test object and collecting vibrations of the test object caused by a physical force; and setting the excitation pattern by controlling the exciter, and converting the physical force signal measured by the first sensor and the vibration signal collected by the second sensor according to the set excitation pattern into a frequency domain signal to calculate the frequency response function of the test object, a sensitivity analysis apparatus for calculating a sensitivity index for a physical external variable of a test object based on a frequency response function, wherein the test object is an object formed with a material arranged to have unidirectionality at a specific angle. Sensitivity analysis apparatus using a frequency response function configured to more accurately analyze the physical properties of object by calculating the sensitivity considering not only the directionality but also various external force patterns for an object having directionality in its internal structure.

In addition, as another example of the prior art for an apparatus and method for analyzing the physical properties of a specific material, such as the damping properties of the above-described carbon composite material, for example, a "Modal damping coefficient measuring apparatus and a modal damping coefficient measuring method using the same" as presented in Korean Patent No. 10-2051746.

More specifically, the aforementioned Korean Patent No. 10-2051746 relates to a modal damping coefficient measuring apparatus and a modal damping coefficient measuring method using the same. The patent above-mentioned discloses including a test object for calculating a modal damping coefficient; an exciter setting an excitation pattern by control and applying a physical force to one side of the test object according to the set excitation pattern; a sensor being in contact with the other side of the test object and collecting a vibration signal generated from the test object by a physical force; and converting the physical force signal applied by the exciter and the vibration signal collected by the sensor into a frequency domain signal to calculate a frequency response function, and extracting the resonance frequency using a peak-picking algorithm based on the frequency response function, Modal damping is configured to accurately analyze the physical properties of the test object by measuring the modal damping coefficient in consideration of not only the input excitation pattern but also temperature and humidity, including a modal damping coefficient calculator that calculates the modal damping coefficient for the resonance frequency.

As described above, in the prior art, various devices and methods for analyzing the physical properties of a specific material have been proposed, but the contents of the prior art as described above have the following limitations.

SUMMARY

One aspect is a method for analyzing the damping characteristics of a carbon composite material using a viscous damping coefficient of carbon fiber and a damping characteristics analysis system of a carbon composite material using the same, thereby solving the problem of the prior art. The problems of the damping characteristics analysis methods of the carbon composite material in the prior art had a limit in which an error occurred in the sensitivity analysis process. A modal damping ratio obtained through a modal test is used to analyze the damping characteristics of carbon composite material, for example, such as CFRP made of carbon fiber, but it should be expressed as a viscous damping coefficient under the assumption that it is a linear system. Since this viscous damping coefficient is not dependent only on the modal damping ratio according to the carbon fiber direction and is also influenced by the resonance frequency variation, the variation in the viscous damping coefficient cannot be expressed only by the modal damping ratio. An error occurred in the sensitivity analysis process because the modal damping ratio includes both the modal characteristics of carbon fiber and binder. To solve these problems described above the sensitivity index is derived by separating the value of the viscous damping coefficient of the carbon fiber that is influenced directly according to the carbon fiber direction from the measured data of the modal damping ratio. The damping characteristics analysis method of a carbon composite material is configured by using only the viscous damping coefficient of carbon fiber configured to analyze the variation in the damping characteristics of the carbon composite material more accurately than the conventional method.

Another aspect is a method for analyzing damping characteristics of carbon composite material using the viscous damping coefficient of carbon fiber and a system for analyzing damping characteristics of carbon composite material using the same. The present disclosure provides that the variation in damping characteristics of the carbon composite material according to the carbon fiber direction was physically accurately analyzed by applying the sensitivity index using only the viscous damping coefficient of the carbon fiber. Assuming that the dynamic characteristics of the carbon composite material appear as linear behavior, the damping characteristics of the carbon composite material are expressed as viscous damping coefficient represented by a parallel combination of the viscous damping coefficient of the carbon fiber and the viscous damping coefficient of the binder matrix. The sensitivity index analyzed how the viscous damping coefficient of the carbon composite material changes according to the carbon fiber direction. In this viscous damping coefficient of the carbon composite material, the viscous damping coefficient related to the binding matrix, which is not changed according to the carbon fiber direction, was eliminated, and the sensitivity index of the carbon composite material was calculated only with the viscous damping coefficient of the carbon fiber. In this way, it was confirmed that the viscous damping coefficient of carbon fiber, which could not be known by the existing analysis method, is proportional to the variation in the resonance frequency (or elastic modulus). Thus, it was possible to analyze the variation in the damping characteristics of the carbon composite material more accurately.

Another aspect is a method of analyzing the damping characteristics of a carbon composite material with the computer or dedicated hardware to analyze the damping characteristics of a carbon composite material using a viscous damping coefficient of the carbon fiber. In the method for analyzing the damping characteristics of a carbon composite material using the viscous damping coefficient of carbon fiber, the process may include: a data collecting step in which processing for collecting various data including each modal parameter measured through a modal test for the carbon composite material to be analyzed is performed; a converting step in which a process of converting the viscous damping coefficient value of the carbon composite material collected in the data collection step into a mass-normalized equivalent viscous damping coefficient is performed; an extracting step in which a process of extracting only the viscous damping coefficient for carbon fiber from the equivalent viscous damping coefficient defined in the converting step is performed; a sensitivity index calculating step of calculating a sensitivity index according to the carbon fiber direction (angle) using the viscous damping coefficient for the carbon fiber extracted in the extracting step; and an analyzing step in which a process of analyzing the damping characteristics of the carbon composite material is performed based on the sensitivity index calculated through the sensitivity index calculating step.

Here, the data collecting step in which the measured values are collected by measuring the viscous damping coefficient of the carbon composite material at a predetermined reference angle, and a predetermined arbitrary angle (θ) through a modal test, respectively, or input processing is performed on the carbon composite material according to the carbon fiber angle measured through a separate input means.

In addition, in the converting step, a process of converting the viscous damping coefficient of the carbon composite material with respect to the predetermined reference angle and the predetermined arbitrary angle (θ) into an equivalent viscous damping coefficient consisting of a parallel combination of the viscous damping coefficient for the carbon fiber and the binding matrix is performed by using the following Formula.

$$\frac{1}{\overline{c}_{def,i}} = \frac{1}{\overline{c}_{F0,i}} + \frac{1}{\overline{c}_{M0,i}}$$

$$\frac{1}{\overline{c}_{eq,i}(\theta)} = \frac{1}{\overline{c}_{F,i}(\theta)} + \frac{1}{\overline{c}_{M0,i}}$$

(Here, $\overline{c}_{def,i}$, $\overline{c}_{F0,i}$ and $\overline{c}_{M0,i}$ represent the viscous damping coefficient of the carbon composite material, the carbon fiber, and the binding matrix with the carbon fiber angle of 0 degrees in the $i^{th}$ mode, respectively, $\overline{c}_{eq,i}(\theta)$ and $\overline{c}_{F,i}(\theta)$ represent the viscous damping coefficient of the carbon composite material and the carbon fiber with the carbon fiber angle θ in the $i^{th}$ mode, respectively)

In addition, in the merging step, the process of merging into a single equation is performed by removing the viscous damping coefficient for the binder matrix from the equivalent viscous damping coefficient defined in the converting step using the following Formula.

$$\left(1 - \frac{\overline{c}_{F0,i}}{\overline{c}_{F,i}(\theta)}\right) = \overline{c}_{F0,i}\left(\frac{1}{\overline{c}_{def,i}} - \frac{1}{\overline{c}_{eq,i}(\theta)}\right)$$

Furthermore, the sensitivity index calculating step is characterized in that the process of calculating the sensitivity index according to the angle (θ) of the carbon fiber for each mode is performed using the following Formula.

$$I_{F,i}(\theta_k) = \frac{\frac{1}{\overline{c}_{def,i}} - \frac{1}{\overline{c}_{eq,i}(\theta_k)}}{\text{norm}\left\{\sum_{k=1}^{N}\left[\frac{1}{\overline{c}_{def,i}} - \frac{1}{\overline{c}_{eq,i}(\theta_k)}\right]\right\}}$$

(Where N means the number of times the carbon fiber angle was increased)

In addition, in the analyzing step, the damping characteristics of the carbon composite material are analyzed based on the sensitivity index calculated for each mode according to the carbon fiber angle through the sensitivity index calculating step and the variation in the viscous damping coefficient according to the carbon fiber angle.

Provided is a computer-readable recording medium on which a program configured to execute a method for analyzing damping characteristics of a carbon composite material using the viscous damping coefficient of a carbon fiber described above on a computer.

Furthermore, provided is a system for analyzing the damping characteristics of a carbon composite material using a viscous damping coefficient of a carbon fiber, characterized by a process for analyzing the damping characteristics of the carbon composite material. The system for analyzing the damping characteristics of a carbon composite material includes: a data collection unit in which a process of collecting various data including each modal parameter measured through a modal test for the carbon composite material to be measured is performed; and a data analysis unit configured to calculate the sensitivity index according to the carbon fiber direction (angle) for the carbon composite material and analyze the damping characteristics based on each data collected through the data collection unit to be performed wherein the data analysis unit is configured to perform a process of analyzing the damping characteristics of the carbon composite material using the method for analyzing the damping characteristics of the carbon composite material using the viscous damping coefficient of the carbon fiber described above.

Here, the analysis system further includes: an output unit configured to display various data, including measured values collected through the data collection unit and analysis results of the data analysis unit, and various information including processing operations and states of the analysis system; a communication unit configured to perform communication in at least one of wired or wireless communication to transmit and receive various data to and from an external device including another analysis system or server; and a control unit configured to perform a process for controlling the overall operation of the analysis system.

In addition, the data collection unit is configured to collect measurement values by measuring each modal parameter through a modal test on the carbon composite material to be measured, or data collected in advance through a modal test is directly input through a separate input means, or configured to transmit by at least one of wired or wireless communication through the communication unit.

In addition, the output unit includes a separate display means including a monitor or a display and is configured to display various data and information including a current state visually.

Furthermore, the control unit is configured to perform a process of transmitting the constructed data to a server, an external device, or another analysis system while controlling the overall operation of the analysis system.

While controlling the overall operation of the analysis system, various data, including measured values collected through the data collection unit and sensitivity indices and analysis results calculated through the data analysis unit, are stored in separate storage means to construct a database for damping characteristics of carbon composite material.

In addition, the analysis system further includes a user terminal for requesting and receiving desired information to/from each of the analysis systems or servers.

Here, the user terminal may be configured using an information processing terminal device including a personal computer (PC) or may be configured by installing a dedicated application on an information communication terminal that may be carried by an individual, including a smartphone, a tablet PC, or a laptop.

As described above, according to the present disclosure, provided is a method for analyzing damping characteristics of carbon composite material using viscous damping coefficient of carbon fiber and a system for analyzing damping characteristics of carbon composite material using thereof. It is possible to physically accurately analyze the variation in the damping characteristics of the carbon composite material according to the carbon fiber direction by separating the viscous damping coefficient of carbon fiber that is directly influenced according to the carbon fiber direction in the modal damping ratio measured data and deriving the sensitivity index. Assuming that the dynamic characteristics of the carbon composite material appear as linear behavior, the damping characteristics of the carbon composite material are expressed as viscous damping coefficient represented by a parallel combination of the viscous damping coefficient of the carbon fiber and the viscous damping coefficient of the binding matrix. The sensitivity index analyzed how the viscous damping coefficient of the carbon composite material changes according to the carbon fiber direction. In this viscous damping coefficient of the carbon composite material, the viscous damping coefficient related to the bonding matrix, which is not changed according to the carbon fiber direction, was eliminated, and the sensitivity index of the carbon composite material was calculated only with the viscous damping coefficient of the carbon fiber. In this way, it was confirmed that the viscous damping coefficient of carbon fiber, which could not be known by the existing analysis method, is proportional to the variation in the resonance frequency (or elastic modulus).

In addition, according to the present disclosure, as described above, the problems of the damping characteristics analysis methods of carbon composite material in the prior art can be solved by providing a damping characteristics analysis method of a carbon composite material and a damping characteristics analysis system of a carbon composite material thereof by using only the viscous damping coefficient of carbon fiber which is configured to analyze the variation in the damping characteristics of the carbon composite material more accurately than the conventional method. Conventionally, a modal damping ratio obtained through a modal test is used to analyze the damping characteristics of carbon composite material, for example, such as CFRP made of carbon fiber, but it should be expressed as a viscous damping coefficient under the assumption that it is a linear system. Since this viscous damping coefficient is not dependent only on the modal damping ratio according to the carbon fiber direction and is also influenced by the resonance frequency variation, the variation in the viscous damping coefficient cannot be expressed only by the modal damping ratio. An error occurred in the sensitivity analysis process because the modal damping ratio includes both the modal characteristics of carbon fiber and binder. To solve these problems described above, the sensitivity index is derived by separating the value of the viscous damping coefficient of the carbon fiber that is influenced directly according to the carbon fiber direction from the measured data of the modal damping ratio.

BRIEF DESCRIPTION OF THE DRAWINGS

FIG. 4 is a table diagram showing modal parameters obtained as a result of performing a modal test under the conditions shown in FIGS. 1 to 3.

DETAILED DESCRIPTION

Figure 1:
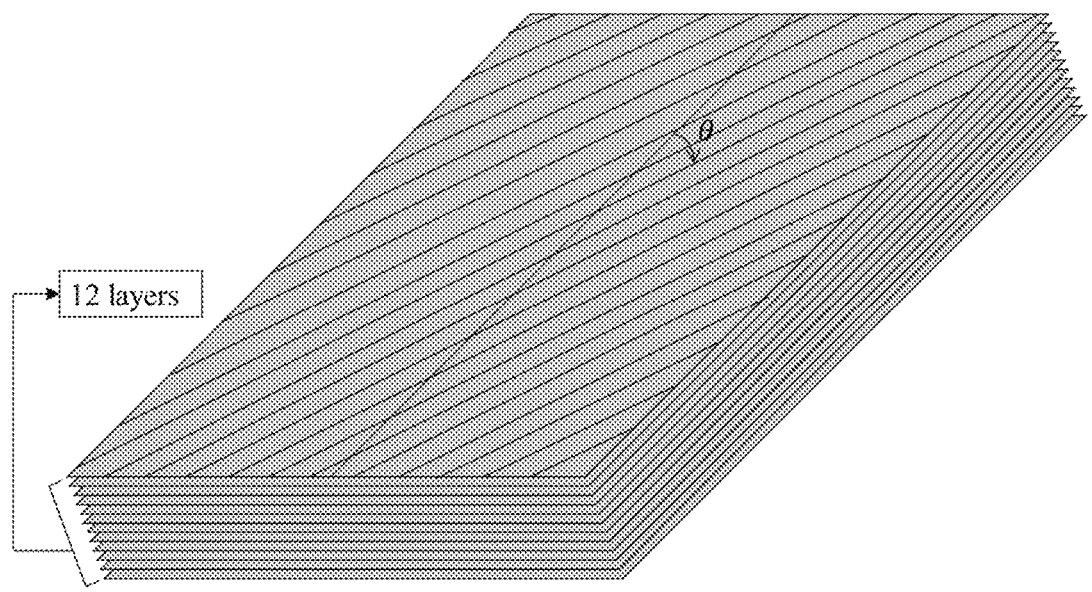
FIG. 1 is a diagram showing a carbon composite material specimen used in a modal test for verifying the damping characteristics analysis method of the carbon composite material using the viscous damping coefficient of the carbon fiber according to an embodiment of the present disclosure.

As described above, in order to apply a carbon composite material such as CFRP, the mechanical and physical properties of the carbon composite material must be accurately identified first. For this purpose, the damping properties of the carbon composite material have been analyzed using a modal damping ratio and sensitivity obtained.

However, the actual damping coefficient of the carbon composite material should be expressed as a viscous damping coefficient under the assumption that it is a linear system. Since the viscous damping coefficient is not dependent only on the modal damping ratio according to the carbon fiber direction but is also influenced by the variation in the resonance frequency, there is a problem that the modal damping ratio alone cannot show a variation in the viscous damping coefficient as in the conventional method.

In addition, in general, since a carbon composite material has a structure in which carbon fiber and a binding matrix bonding the same are very tightly bonded, the modal damping ratio obtained through a modal test for the carbon composite material includes both modal characteristics of carbon fiber and binding matrix. Therefore, the existing methods for analyzing the damping characteristics of carbon composite material using the modal damping ratio have a problem in that an error occurs in the sensitivity analysis result due to the modal value of the binder without variation in the differentiation process for sensitivity analysis.

Therefore, in order to solve the limitations of the methods of analyzing the damping characteristics of the carbon composite material using the modal damping ratio of the prior art, it is desirable to present a new method of physically and accurately analyzing the damping characteristics of the carbon composite material, in which the variation in damping characteristics can be physically and accurately analyzed by separating only the viscous damping coefficient of carbon fiber from the modal damping coefficient for the entire carbon composite material to calculate the sensitivity index based on the carbon fiber viscous damping coefficient according to the carbon fiber direction. Apparatuses or methods that satisfy all such demands have not yet been proposed.

A modal damping ratio obtained through a modal test is used to analyze the damping characteristics of carbon composite material, such as Carbon-Fiber-Reinforced Plastic (CFRP) made of carbon fiber, but it should be expressed as a viscous damping coefficient under the assumption that it is a linear system. Since this viscous damping coefficient is not dependent only on the modal damping ratio according to the carbon fiber direction and is also influenced by the resonance frequency variation, the variation in the viscous damping coefficient cannot be expressed only by the modal damping ratio. An error occurred in a sensitivity analysis process because the modal damping ratio includes both the modal characteristics of carbon fiber and binder. A sensitivity index is derived by separating the value of the viscous damping coefficient of the carbon fiber that is influenced directly according to the carbon fiber direction from the measured data of the modal damping ratio. The damping characteristics analysis method of a carbon composite material is configured by using only the viscous damping coefficient of carbon fiber which is configured to analyze the variation in the damping characteristics of the carbon composite material more accurately than the conventional method.

In addition, the present disclosure, as described above, relates to a method for analyzing the damping characteristics of a carbon composite material in which the variation in damping characteristics of the carbon composite material according to the carbon fiber direction was physically accurately analyzed by applying the sensitivity index using only the viscous damping coefficient of the carbon fiber. Assuming that the dynamic characteristics of the carbon composite material appear as linear behavior, the damping characteristics of the carbon composite material are expressed as viscous damping coefficient represented by a parallel combination of the viscous damping coefficient of the carbon fiber and the viscous damping coefficient of the binding matrix. The sensitivity index analyzed how the viscous damping coefficient of the carbon composite material changes according to the carbon fiber direction. In this viscous damping coefficient of the carbon composite material, the viscous damping coefficient related to the bonding matrix, which is not changed according to the carbon fiber direction, was eliminated, and the sensitivity index of the carbon composite material was calculated only with the viscous damping coefficient of the carbon fiber. In this way, it was confirmed that the viscous damping coefficient of carbon fiber, which could not be known by the existing analysis method, is proportional to the variation in the resonance frequency (or elastic modulus). Thus, it was possible to analyze the variation in the damping characteristics of the carbon composite material more accurately.

Hereinafter, with reference to the accompanying drawings, a method for analyzing the damping characteristics of a carbon composite material using the viscous damping coefficient of the carbon fiber according to the present disclosure and a specific example of a system for analyzing the damping characteristics of a carbon composite material using the same will be described.

Here, it should be noted that the content described below is only one embodiment for carrying out the present disclosure, and the present disclosure is not limited to the content of the embodiment described below.

In addition, it should be noted that the following description of embodiments of the present disclosure has been omitted to simplify the description of parts that are the same as or similar to the contents of the prior art or that may be easily understood and implemented at the level of those skilled in the art.

That is, as will be described later, The present disclosure relates to a method for analyzing the damping characteristics of a carbon composite material using a viscous damping coefficient of carbon fiber and a damping characteristics analysis system of a carbon composite material using the same. A modal damping ratio obtained through a modal test is used to analyze the damping characteristics of carbon composite material, for example, such as CFRP made of carbon fiber, but it should be expressed as a viscous damping coefficient under the assumption that it is a linear system. Since this viscous damping coefficient is not dependent only on the modal damping ratio according to the carbon fiber direction and is also influenced by the resonance frequency variation, the variation in the viscous damping coefficient cannot be expressed only by the modal damping ratio. An error occurred in the sensitivity analysis process because the modal damping ratio includes both the modal characteristics of carbon fiber and binder. To solve these problems described above, the sensitivity index is derived by separating the value of the viscous damping coefficient of the carbon fiber that is influenced directly according to the carbon fiber direction from the measured data of the modal damping ratio. The damping characteristics analysis method of a carbon composite material is configured by using only the viscous damping coefficient of carbon fiber configured to analyze the variation in the damping characteristics of the carbon composite material more accurately than the conventional method.

In addition, the present disclosure, as will be described later, relates to a method for analyzing the damping characteristics of a carbon composite material in which the variation in damping characteristics of the carbon composite material according to the carbon fiber direction was physically accurately analyzed by applying the sensitivity index using only the viscous damping coefficient of the carbon fiber. Assuming that the dynamic characteristics of the carbon composite material appear as linear behavior, the damping characteristics of the carbon composite material are expressed as viscous damping coefficient represented by a parallel combination of the viscous damping coefficient of the carbon fiber and the viscous damping coefficient of the binding matrix. The sensitivity index analyzed how the viscous damping coefficient of the carbon composite material changes according to the carbon fiber direction. In this viscous damping coefficient of the carbon composite material, the viscous damping coefficient related to the bonding matrix, which is not changed according to the carbon fiber direction, was eliminated, and the sensitivity index of the carbon composite material was calculated only with the viscous damping coefficient of the carbon fiber. In this way, it was confirmed that the viscous damping coefficient of carbon fiber, which could not be known by the existing analysis method, is proportional to the variation in the resonance frequency (or elastic modulus). It was possible to analyze the variation in the damping characteristics of the carbon composite material more accurately.

Subsequently, with reference to the drawings, a method for analyzing damping characteristics of a carbon composite material using a viscous damping coefficient of a carbon fiber according to the present disclosure and a system for analyzing damping characteristics of a carbon composite material using the same will be described.

Here, before explaining the method for analyzing the damping characteristics of a carbon composite material using the viscous damping coefficient of carbon fiber according to the present disclosure, the carbon composite material and the viscous damping coefficient will be described. Among the advantages of carbon composite material such as CFRP, the damping coefficient is large, and by accurately understanding this damping coefficient, important information can be provided for designing the damping characteristics of the carbon composite material. That is, in general, a carbon composite material is largely divided into a carbon fiber and a binding matrix bonding the carbon fiber, and since these two elements are very tightly bonded, the viscous damping coefficient of the carbon composite material can be expressed as a parallel combination of each viscous damping coefficient dependent on the carbon fiber and the binder.

Here, although the carbon fiber direction is changed, the viscous damping coefficient by the binder matrix is not changed, and thus the viscous damping coefficient value of the entire carbon composite material varies only depending on the variation in the viscous damping coefficient related to the carbon fiber.

In addition, when the variation in the viscous damping coefficient value of the entire carbon composite material for the carbon fiber direction is expressed in differential form, the sensitivity analysis results for the carbon fiber direction do not have a physical tendency because the constant binder-related viscous damping coefficient, which does not change, affects parallel combinations.

Therefore, in the present disclosure, as will be described later, the damping characteristics of the carbon composite material are expressed as a viscous damping coefficient under the condition that it is reasonable to assume the dynamic properties of the carbon composite material as a linear behavior. After separating the viscous damping coefficient of the carbon composite material into the viscous damping coefficient of the carbon fiber and the viscous damping coefficient of the binding matrix, it was confirmed that the sensitivity of the carbon fiber was proportional to the variation in the resonance frequency (or elastic modulus) of the carbon fiber through sensitivity analysis according to the carbon fiber direction for the viscous damping coefficient of the separated carbon fiber. According to these results, a method of analyzing the damping characteristics of a carbon composite material was proposed to physically and accurately analyze the variation in the damping characteristics of the carbon composite material according to the carbon fiber direction by applying the sensitivity index using only the viscous damping coefficient of the carbon fiber.

In addition, in the embodiment of the present disclosure described below, all viscous damping coefficients are values normalized with a modal mass of the corresponding order, that is, for example, the viscous damping coefficient in the $i^{th}$ mode in the 1st degree of freedom (degrees-of-free) system is a value obtained by dividing 1 by the corresponding modal mass ($m_i$).

More specifically, as described above, CFRP consists of two main materials: a carbon fiber material and a binding matrix material, and the carbon fiber and binding matrix are merged into a single composite structure during the manufacturing process, i.e., hot pressing. When combined into a single composite structure, the viscous damping coefficient of the composite is not simply the summation of the viscous damping coefficient of each material.

That is, when the CFRP structure can be allowed to be a linear system, the viscous damping coefficient Ci can be assumed to be a parallel combination of the carbon fiber and the binding matrix. As the carbon fiber angle increased, the viscous damping coefficient of the binding matrix did not change, but the viscous damping coefficient of the carbon fiber changed.

In addition, the combination of the two materials can be assumed to be parallel in a linear system because CFRP is manufactured as a composite structure using carbon fiber and a binding matrix. When the $i^{th}$ mass-normalized viscous damping coefficient is defined as $\overline{c}_{def,i}$ at the reference angle of the carbon fiber, the viscous damping coefficient may be represented by two mass normalized viscous damping coefficients, that is, equivalent viscous damping coefficient derived from the carbon fiber ($\overline{C}_{F,i}$) and the binder matrix ($\overline{C}_{M,i}$), as shown in Formula 1 below.

$$\frac{1}{\overline{c}_{def,i}} = \frac{1}{\overline{c}_{F0,i}} + \frac{1}{\overline{c}_{M0,i}} \quad \text{[Formula 1]}$$

In addition, when the carbon fiber angle increases from the reference angle to θ, the equivalent mass normalized viscous damping coefficient ($\overline{C}_{eq,i}(\theta)$), as shown in Formula 2 below, may be expressed in a form similar to Formula 1 above using a constant mass normalized viscous damping coefficient ($\overline{C}_{M,i}$) of binding matrix and the mass normalized viscous damping coefficient of carbon fiber ($\overline{C}_{F,i}(\theta)$).

$$\frac{1}{\overline{c}_{eq,i}(\theta)} = \frac{1}{\overline{c}_{F,i}(\theta)} + \frac{1}{\overline{c}_{M0,i}} \quad \text{[Formula 2]}$$

Here, in the above [Formula 1] and [Formula 2], $\overline{c}_{def,i}$, $\overline{c}_{F0,i}$ and $\overline{c}_{M0,i}$ represent the viscous damping coefficient of the carbon composite material, the carbon fiber, and the binding matrix with the carbon fiber angle of 0 degrees in the $i^{th}$ mode, respectively, $C_{eq,i}(\theta)$ and $\overline{C}_{F,i}(\theta)$ represent the viscous damping coefficient of the carbon composite material and the carbon fiber with the carbon fiber angle θ in the i-th mode, respectively.

At this time, in order to maintain the same viscous damping coefficient ($\overline{C}_{M0,i}$) value of the binding matrix in two different carbon composite materials, only the carbon fiber direction may be different, and other conditions may be the same to keep the same value.

Subsequently, in the above [Formula 1] and [Formula 2], when the constant viscous damping coefficient value ($\overline{C}_{M0,i}$) of the binder matrix that exists in common is eliminated and merged into one equation, it can be expressed as the following [Formula 3].

$$\left(1 - \frac{\overline{c}_{F0,i}}{\overline{c}_{F,i}(\theta)}\right) = \overline{c}_{F0,i}\left(\frac{1}{\overline{c}_{def,i}} - \frac{1}{\overline{c}_{eq,i}(\theta)}\right) \quad \text{[Formula 3]}$$

Here, in the above [Formula 3], the left term is a formulation of the relative error between the viscous damping coefficient of the carbon fiber, the increase in carbon fiber angle θ, and the reference angle.

In addition, in the above [Formula 3], the right term is the viscous damping coefficient of the carbon composite material at the reference angle and the increased carbon fiber angle θ, $\overline{c}_{def,i}$ and $\overline{C}_{eq,i}(\theta)$ respectively, which can be obtained from the experimental modal test.

In addition, in the $i^{th}$ mode, the sensitivity according to the carbon fiber direction, that is, the carbon fiber angle θ, with respect to the viscous damping coefficient of the carbon composite material can be obtained through direct partial derivative as shown in the following [Formula 4].

$$\frac{\Delta c_i(\theta)}{\Delta \theta} = \frac{\Delta(2m_i\omega_{n,i}\zeta_i)}{\Delta \theta} = 2m_i\left[\zeta_i\frac{\Delta \omega_{n,i}}{\Delta \theta} + \omega_n\frac{\Delta \zeta_i}{\Delta \theta}\right] \overline{c}_i = \frac{c_i}{m_i} \quad \text{[Formula 4]}$$

Here, in the above [Formula 4], m is mass, $\omega_n$ is a resonance frequency, $\xi$ is a modal damping ratio, and c represents a viscous damping coefficient, respectively.

The above [Formula 4] is a general formula using the derivation of the equivalent viscous damping coefficient of the CFRP structure, but since the viscous damping coefficient of the binding matrix $\overline{c}_{M0,i}$ does not change according to the carbon fiber angle, there is a limitation in that the direct derivative of the equivalent viscous damping coefficient cannot be expressed accurately.

That is, the constant value of the viscous damping coefficient of the binding matrix may distort the sensitivity result in [Formula 4]. As a result, the proposed sensitivity analysis of the viscous damping coefficient for only carbon fiber is more reasonable for identifying variations in the damping coefficient with the increase in the carbon fiber angle.

More specifically, the above [Formula 4] has the advantage of deriving a sensitivity result that accurately expresses the variation amount of the viscous damping coefficient for the carbon composite material that changes as the carbon fiber direction is increased. Still, in fact, as shown in the above [Equation 2], since the viscous damping coefficient is composed of a parallel combination of the viscous damping coefficient of the carbon fiber and the binding matrix, there is a limit to expressing the actual variation in the viscous damping coefficient of the carbon fiber with sensitivity.

Therefore, in the present disclosure, in order to overcome the limitations of the existing sensitivity analysis method as described above, the sensitivity index value was derived as shown in [Formula 5] by using [Formula 3], which is a relational expression regarding the viscous damping coefficient of carbon fiber.

$$I_{F,i}(\theta_k) = \frac{\frac{1}{\overline{c}_{def,i}} - \frac{1}{\overline{c}_{eq,i}(\theta_k)}}{\text{norm}\left\{\sum_{k=1}^{N}\left[\frac{1}{\overline{c}_{def,i}} - \frac{1}{\overline{c}_{eq,i}(\theta_k)}\right]\right\}} \quad \text{[Formula 5]}$$

In addition, for comparison with the present disclosure, for comparison with the present disclosure, if the sensitivity index of [Formula 4] is expressed similarly to [Formula 5] described above, it can be expressed as [Formula 6] below.

$$I_{eq,i}(\theta_k) = \frac{\zeta_{avg,k}\frac{\Delta \omega_{n,i}}{\Delta \theta_k} + \omega_{avg,k}\frac{\Delta \zeta_i}{\Delta \theta_k}}{\text{norm}\left\{\sum_{k=1}^{N}\left[\zeta_{avg,k}\frac{\Delta \omega_{n,i}}{\Delta \theta_k} + \omega_{avg,k}\frac{\Delta \zeta_i}{\Delta \theta_k}\right]\right\}} \quad \text{[Formula 6]}$$

Here, in the above [Formula 5] and [Formula 6], N is the number of times the carbon fiber angle is increased (number of times), $\zeta_{avg,k}$ is the averaged modal damping ratio, $\omega_{avg}$, denotes averaged resonance frequencies at $(k-1)^{th}$ and $k^{th}$ angles ($k=0$ is a reference angle), respectively.

More specifically, in practice, the sensitivity index for different carbon fiber angles in a specific resonance mode is proposed under the discrete increase in the carbon fiber angle. The derivative of the mass-normalized viscous damping coefficient for the carbon fiber angle increase $\theta_k$ and $i^{th}$ mode can be derived as the sensitivity index $I_{eg,i}(\theta_k)$ using the averaged modal damping ratio $\xi_{avg,k}$ and the averaged resonance frequency $\omega_{avg,k}$ in the $(k-1)^{th}$ angle and $k^{th}$ angle ($k=0$ is the reference angle) as shown in [Formula 6]

In addition, the sensitivity index for a specific carbon fiber angle ($\theta_k$) is formulated by dividing the 2-norm of all sets of sensitivity values, and the sensitivity index of carbon fiber only is also derived by dividing the 2 norm of all sets of relative error values as shown in [Formula 5]

In addition, $I_{F,i}(\theta_k)$ indicates the sensitivity of the carbon fiber to angle increase $\theta_k$ and $i^{th}$ mode. The invariant variables, 2mi in [Formula 4] and $\overline{C}_{F0,i}$ in [Formula 3] were eliminated for the final form in the sensitivity index.

In conclusion, the main content proposed by the present disclosure is [Formula 3], which is expressed only by the viscous damping coefficient of carbon fiber by removing the term of the binding matrix-related viscous damping coefficient, which does not change according to the carbon fiber direction, and [Formula 5] representing the sensitivity index using thereby.

Subsequently, the results of performing a modal test using a carbon composite material will be described to verify the above contents.

That is, to experimentally verify the above description, the present inventors measured modal parameters, including a resonance frequency and a modal damping ratio, through a modal test using a carbon composite material.

Here, the method of extracting the modal parameter is experimental content presented in "A method for analyzing dynamic mode variation of anisotropic material and an analysis device using the same" of Korean Patent No. 10-2021-0075856, filed on Jun. 11, 2021, by the present inventors, was applied as it is.

Figure 2:
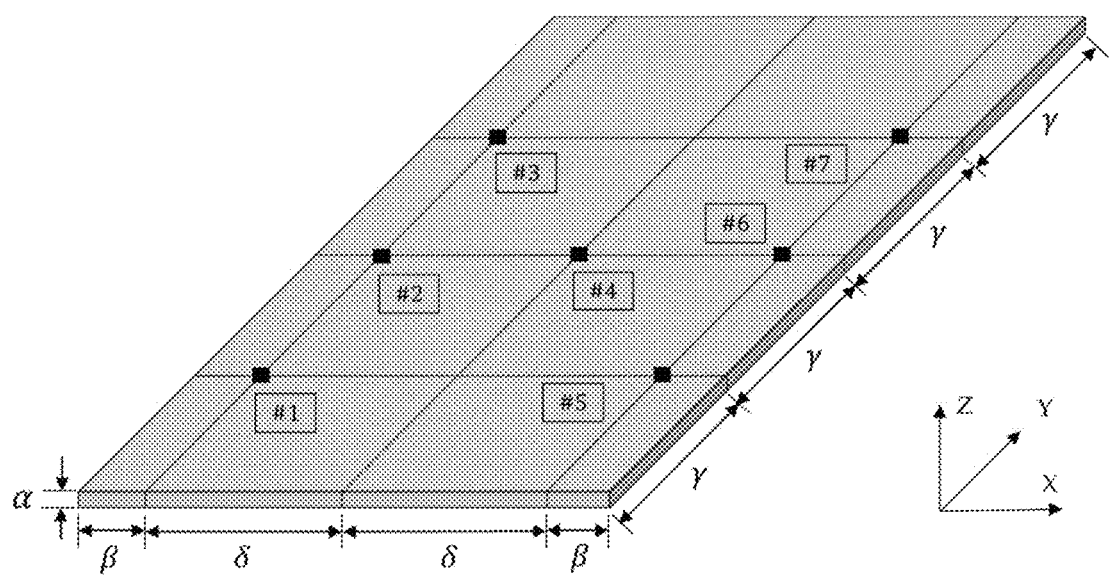
FIG. 2 is a diagram showing the length information of the carbon composite material specimen applied to the modal test for verification of the present disclosure and the attachment position of the acceleration sensor, respectively.
Figure 3:
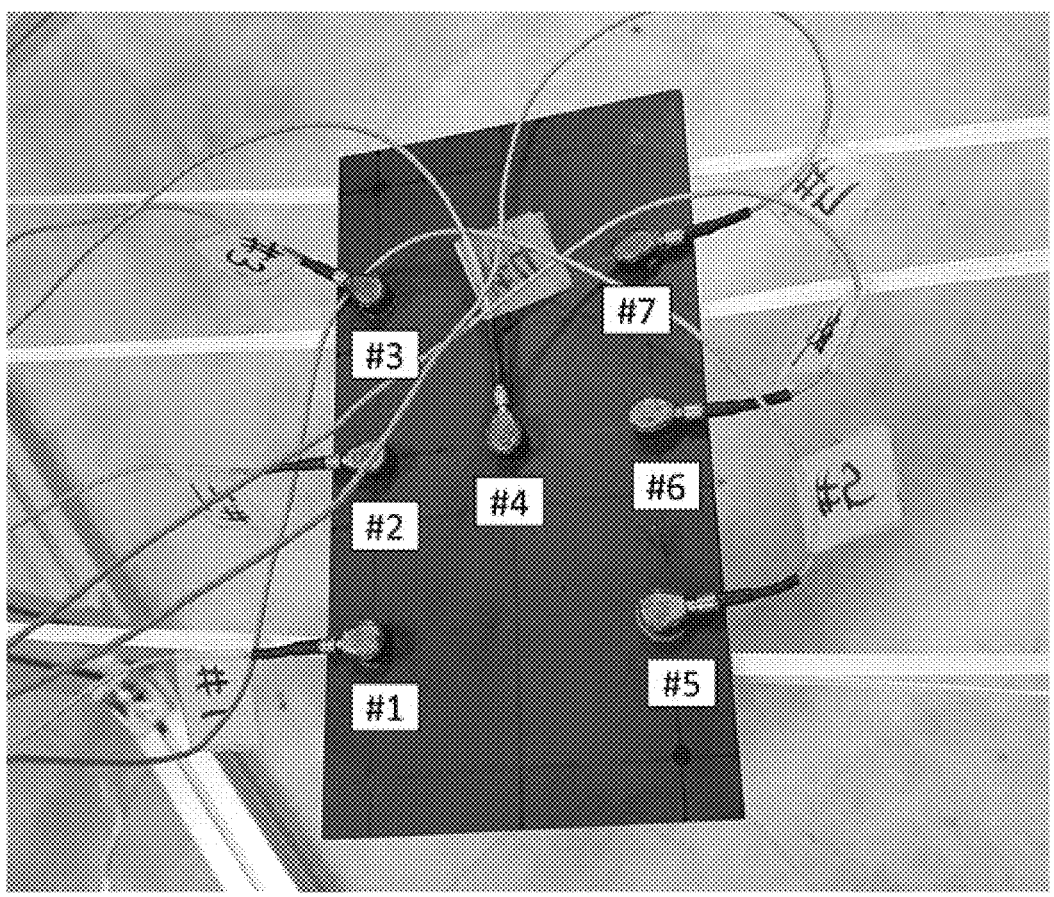
FIG. 3 is a diagram showing a state in which a modal test is actually performed by hanging a carbon composite material specimen to which an acceleration sensor is attached to a rubber band with low rigidity in order to extract modal parameters.

More specifically, referring to FIGS. 1 to 3, FIG. 1 is a diagram showing a specimen of a carbon composite material consisting of 12 layers used in a modal test to verify a method for analyzing damping characteristics of a carbon composite material using a viscous damping coefficient of a carbon fiber according to an embodiment of the present disclosure.

In the carbon composite material specimen shown in FIG. 1, $\theta$ represents the direction (angle) of the carbon fiber, and in this experiment, five carbon composite material specimens with $\theta$ of 0 degrees, 30 degrees, 45 degrees, 60 degrees, and 90 degrees, respectively, were used.

Also, referring to FIG. 2, FIG. 2 is a diagram showing length information of a carbon composite material specimen applied to a modal test to verify the present disclosure and an attachment position of an acceleration sensor, respectively.

In FIG. 2, $\alpha=3$ mm, $\beta=10$ mm, $\gamma=37.5$ mm, and $\delta=30$ mm, and #1 to #7 indicate the attachment positions of the acceleration sensors, respectively.

In addition, referring to FIG. 3, FIG. 3 is a diagram showing a state in which a modal test is performed by hanging a carbon composite material specimen with an acceleration sensor attached to that on a rubber band with low rigidity to extract modal parameters.

Furthermore, referring to FIG. 4, FIG. 4 is a table showing modal parameters extracted by performing a modal test under the same conditions as described above.

That is, as a result of performing the modal test under the conditions as described above, each modal parameter was extracted as shown in the table of FIG. 4, and these results are also specified in the above specification of application (Korean Patent No. 10-2021-0075856).

Continuingly, referring to FIGS. 5A to 5E, FIGS. 5A to 5E are diagrams showing the results of each analysis performed by using [Formula 5], which is the sensitivity index proposed in the present disclosure based on the information as described above, and [Formula 6], which is a sensitivity index including a viscous damping coefficient value of a binder matrix as a comparison.

Here, in the comparison result shown in FIGS. 5A to 5E, the analysis was performed by limiting the mode to five modes as shown in the table of FIG. 4, black indicates the sensitivity value to be compared [Formula 6] is applied, and grey indicates the results according to [Formula 5] proposed in the present disclosure are respectively shown.

Figure 5A:
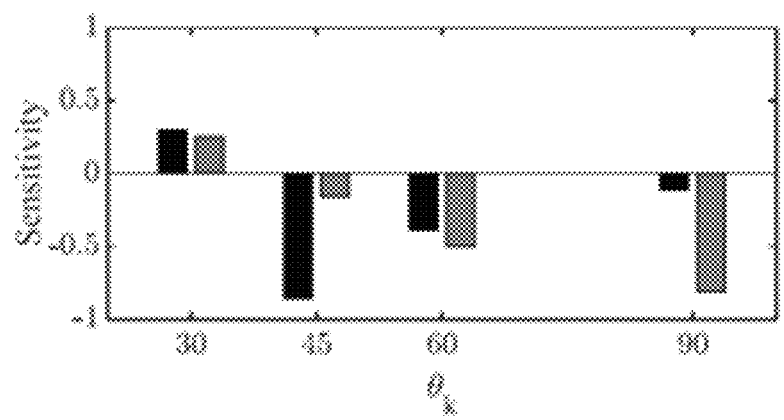
FIGS. 5A to 5E are diagrams showing the results of each analysis using the sensitivity index proposed in the present disclosure and the existing sensitivity index, including the value of the viscosity damping coefficient of the binder matrix.
Figure 5B:
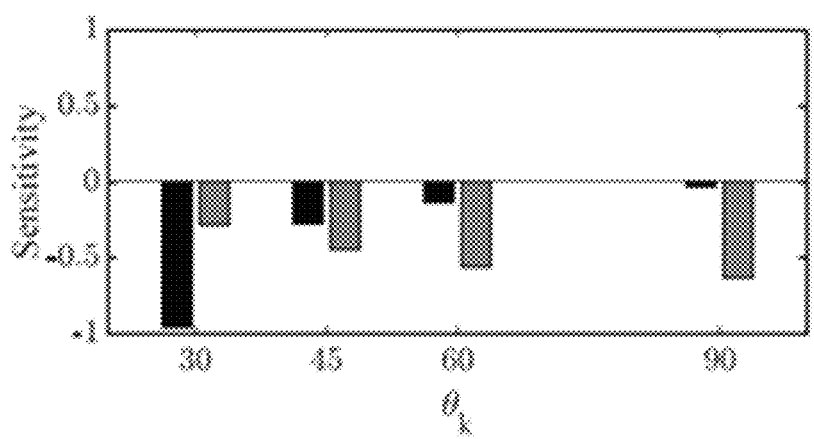
Figure 5C:
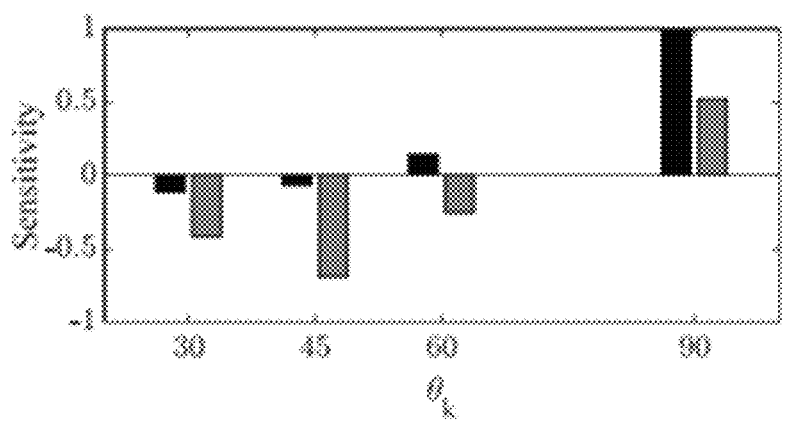
Figure 5D:
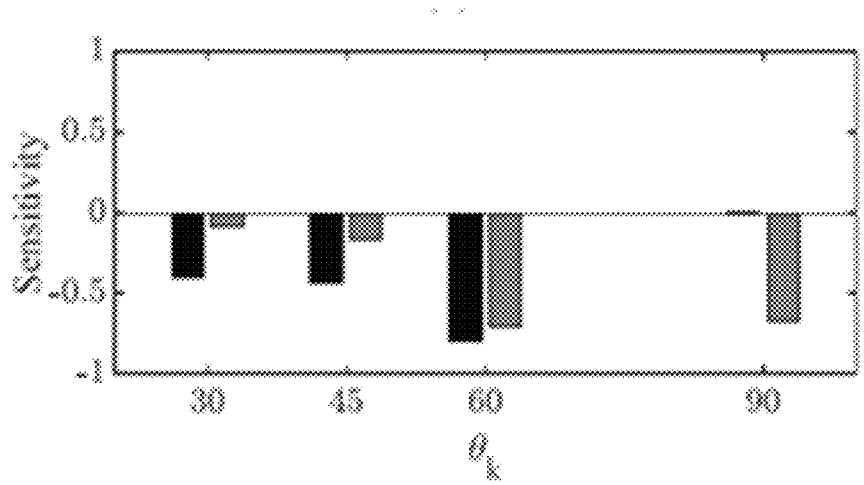
Figure 5E:
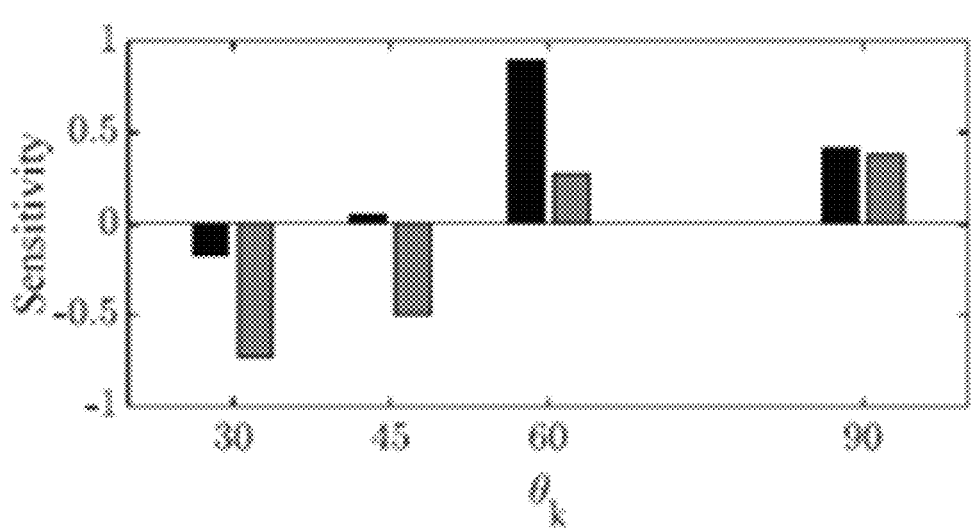

In addition, in FIGS. 5A to 5E, FIG. 5A is a primary bending mode, FIG. 5B is a primary twisting mode, FIG. 5C is a secondary bending mode, FIG. 5D is a secondary bending mode, FIG. 5E is a tertiary bending mode, and $\theta_0=0$ degree (default), $\theta_1=30$ degrees, $\theta_2=45$ degrees, $\theta_3=60$ degrees, $\theta_4=90$ degrees.

As shown in FIGS. 5A to 5E, when comparing the respective sensitivity index values, it can be confirmed that the sensitivity values (black) according to the conventional method do not show any physical similarity to the characteristics of the specimens, but on the other hand, the sensitivity values (grey) proposed in the present disclosure shows the same tendency as the relative error of the resonance frequency.

That is, referring to FIGS. 6A to 6E, FIGS. 6A to 6E are diagrams showing relative errors of resonance frequency (an error according to the carbon fiber direction (angle) based on $\theta 0$) for five modes, respectively.

Figure 6A:
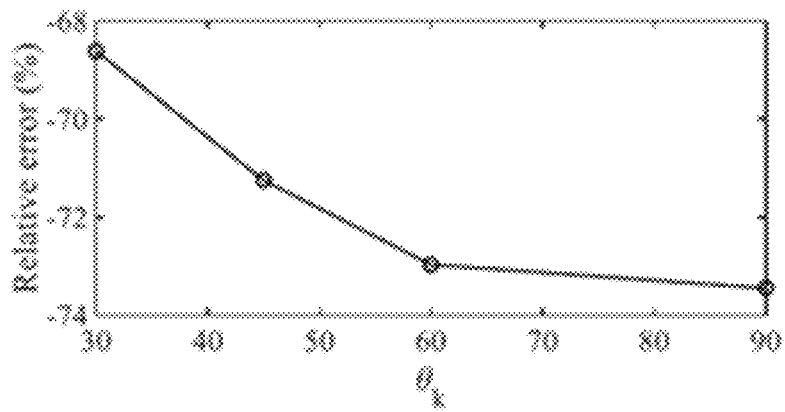
FIGS. 6A to 6E are diagrams showing the relative errors of resonance frequency for five modes, respectively.
Figure 6B:
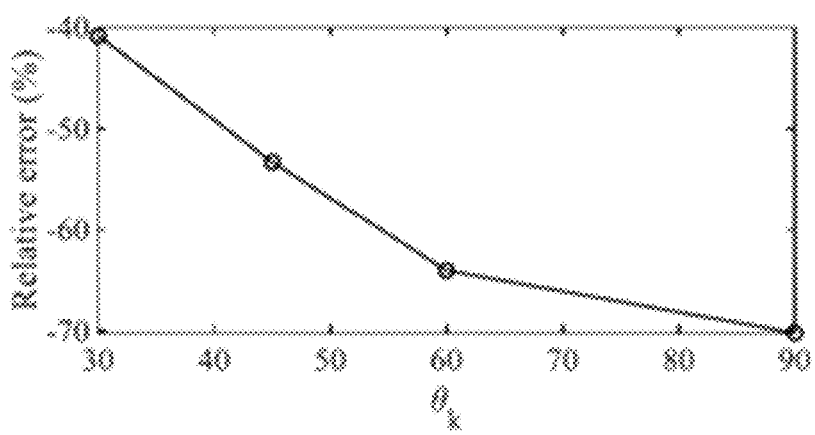
Figure 6C:
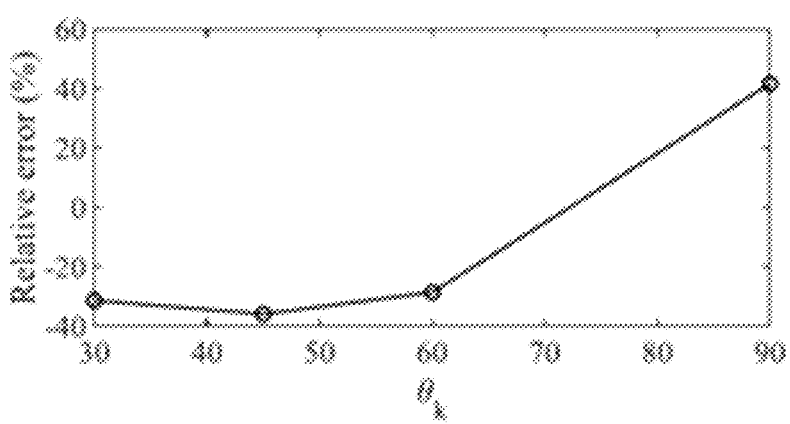
Figure 6D:
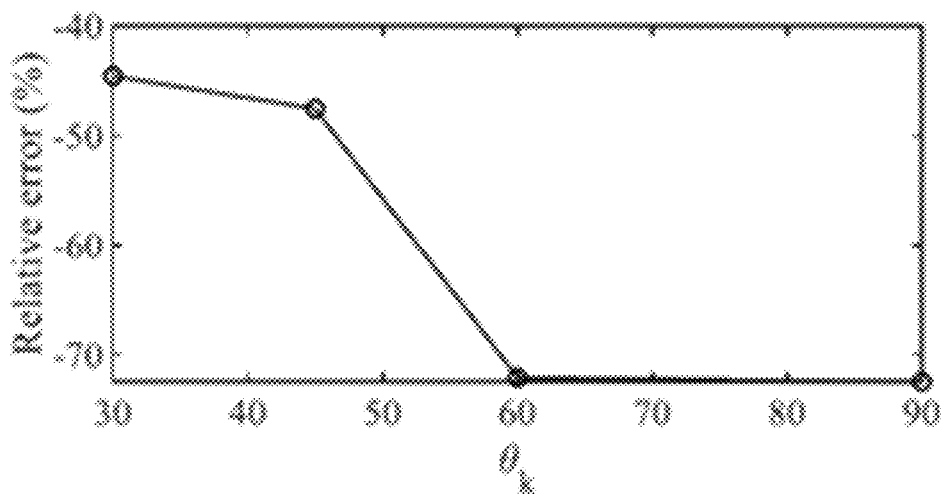
Figure 6E:
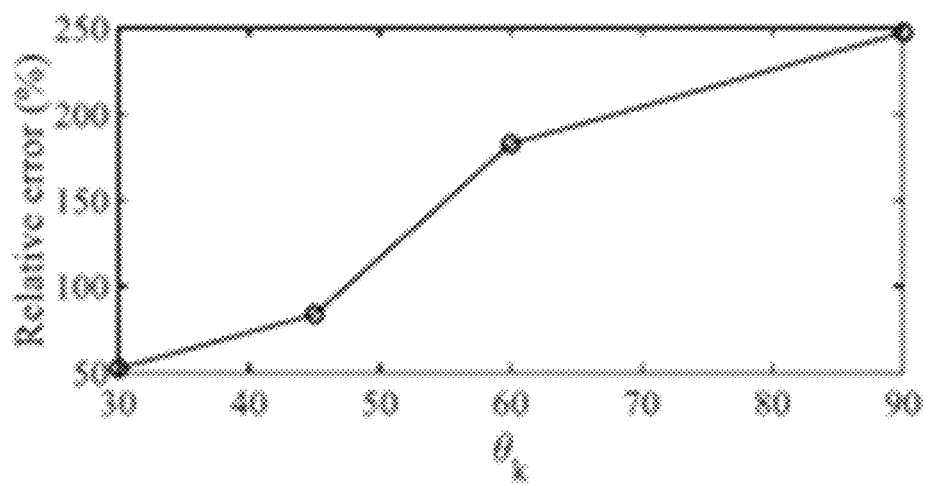

In FIGS. 6A to 6E, similarly to FIGS. 5A to 5E, FIG. 6A is a primary bending mode, FIG. 6B is a primary twisting mode, FIG. 6C is a secondary bending mode, FIG. 6D is a secondary bending mode, and FIG. 6E represents a tertiary bending mode.

As shown in FIGS. 5A to 6E, it can be confirmed that the tendency of FIGS. 6A to 6E and the tendency of the grey part of FIGS. 5A to 5E are consistent. From these results, it can be confirmed that the method presented in this disclosure has sufficient validity and value.

From the above, according to the present disclosure, after separating the viscous damping coefficient of the carbon composite material into the viscous damping coefficient of the carbon fiber and the viscous damping coefficient of the binding matrix, it was confirmed that the sensitivity of the carbon fiber was proportional to the variation in the resonance frequency (or elastic modulus) of the carbon fiber through sensitivity analysis according to the carbon fiber direction for the viscous damping coefficient of the carbon fiber. According to these results, the variation in the damping characteristics of the carbon composite material according to the carbon fiber direction by applying the sensitivity index using only the viscous damping coefficient of the carbon fiber can be physically accurately analyzed.

Here, in the above-described embodiment of the present disclosure, the present disclosure has been described by taking the case of analyzing the damping characteristics of carbon fiber reinforced plastic (CFRP) as a carbon composite material applied for the analysis of the damping characteristics as an example, but the present disclosure is not necessarily limited only to the above-described embodiments, that is, the present disclosure can be applied in the same or similar manner to other composite materials other than the above-described CFRP, without departing from the spirit and essence of the present disclosure. It should be noted that various modifications and variations are applicable as needed by those skilled in the art.

Therefore, it is possible to easily implement the damping characteristics analysis method of the carbon composite material using the viscous damping coefficient of the carbon fiber and the damping characteristics analysis system of the carbon composite material using the same from the above content.

Figure 7:
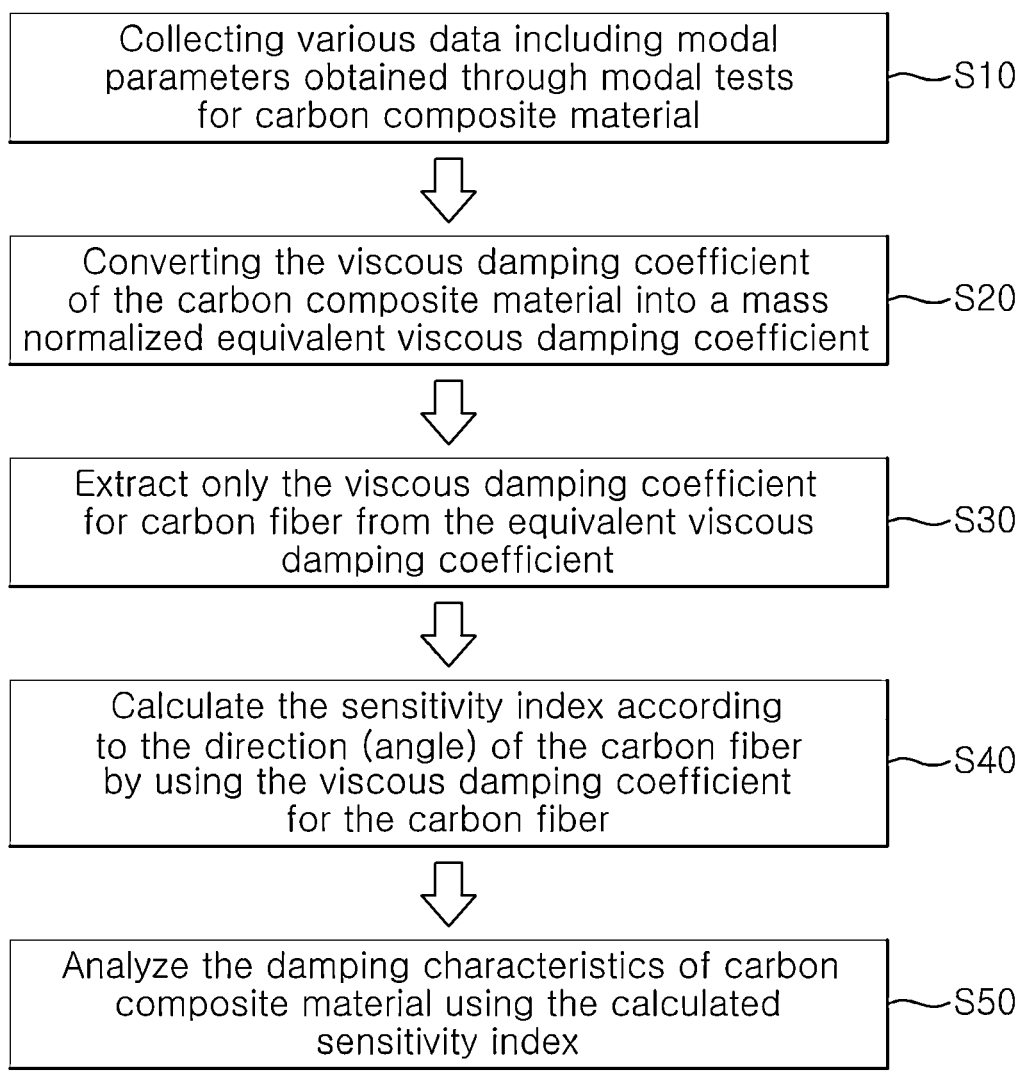
FIG. 7 is a flowchart schematically showing the overall configuration of a method for analyzing the damping characteristics of a carbon composite material using the viscous damping coefficient of carbon fiber according to an embodiment of the present disclosure.

Subsequently, referring to FIG. 7, FIG. 7 is a flowchart schematically showing the overall configuration of a method for analyzing the damping characteristics of a carbon composite material using the viscous damping coefficient of carbon fiber according to an embodiment of the present disclosure.

As shown in FIG. 7, the method for analyzing the damping characteristics of a carbon composite material using the viscous damping coefficient of carbon fiber according to an embodiment of the present disclosure is largely divided into steps for a carbon composite material to be analyzed, such as CFRP: a data collecting step S10 in which processing for collecting various data including each modal parameter measured through a modal test for the carbon composite material to be analyzed is performed; a converting step S20 in which a process of converting the viscous damping coefficient value of the carbon composite material collected in the data collecting step S10 into a mass-normalized equivalent viscous damping coefficient is performed; an extracting step S30 in which a process of extracting only the viscous damping coefficient for carbon fiber from the equivalent viscous damping coefficient defined in the converting step S20 is performed; a sensitivity index calculating step S40 of calculating a sensitivity index according to the carbon fiber direction (angle) using the viscous damping coefficient for the carbon fiber extracted in the extracting step S30; and an analyzing step S50 in which a process of analyzing the damping characteristics of the carbon composite material is performed based on the sensitivity index calculated through the sensitivity index calculating step S40. A series of processing processes including the steps described above may be configured to perform by the computer or dedicated hardware.

Here, in the data collecting step S10, as described above with reference to FIGS. 1 to 4, the input processing may be configured to be performed by collecting a measured value with measuring a viscous damping coefficient of a carbon composite material at a reference angle (e.g., 0 degrees) and a changed angle (θ), or receiving the values of the viscous damping coefficient according to the carbon fiber angle measured in advance through a modal test with a separate input means.

In addition, the above-described converting step S20, using the above [Formula 1] and [Formula 2], may be configured to perform the process that each viscous damping coefficient for the reference angle and an arbitrary angle θ of carbon fiber is expressed as an equivalent viscous damping coefficient consisting of a parallel combination of the viscous damping coefficient for the carbon fiber and the viscous damping coefficient for the binding matrix.

In addition, in the merging step S30, the process of merging into an equation representing the relative error between the respective viscous damping coefficient of carbon fiber at reference angle and the respective viscous damping coefficient of carbon fiber at an arbitrary angle θ, and the equivalent viscous damping coefficient of the carbon composite material may be performed by eliminating the viscous damping coefficient for the binding matrix from the respective equivalent viscous damping coefficient for the reference angle and the arbitrary angle θ of the carbon fiber defined in the converting step S20.

Furthermore, in the above-mentioned sensitivity index calculating step S40, using the above [Formula 5], the process of calculating a sensitivity index by applying a partial differential to the equation obtained in the above-described merging step S30 may be performed.

In addition, in the above-described analyzing step S50, using the sensitivity index calculated through the sensitivity index calculating step S40, the process of analyzing the damping characteristics of the carbon composite material may be performed through the tendency of the sensitivity index calculated for each carbon fiber direction (angle) and mode.

Therefore, it is possible to easily implement the damping characteristics analysis method of the carbon composite material using the viscous damping coefficient of the carbon fiber according to the embodiment of the present disclosure by executing the series of processing steps as described above in the computer or dedicated hardware. In addition, by using this, it is possible to easily implement an analysis system that analyzes the damping characteristics of carbon composite material.

Figure 8:
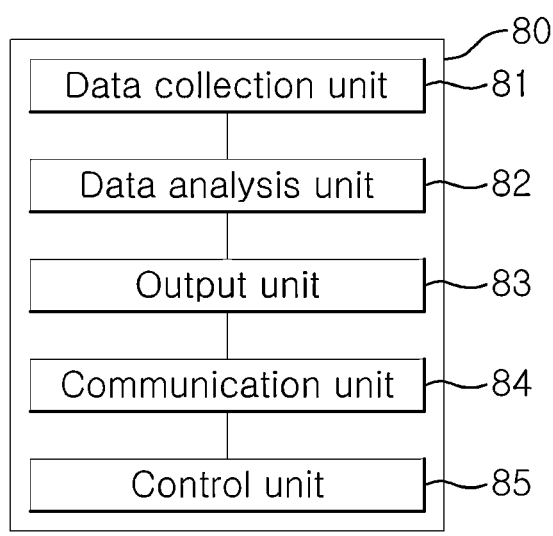
FIG. 8 is a block diagram schematically showing the overall configuration of a system for analyzing damping characteristics of a carbon composite material according to an embodiment of the present disclosure.

That is, referring to FIG. 8, FIG. 8 is a block diagram schematically showing the overall configuration of the damping characteristics analysis system 80 of the carbon composite material according to an embodiment of the present disclosure.

As shown in FIG. 8, the damping characteristics analysis system 80 of the carbon composite material according to the embodiment of the present disclosure may be performed, which is largely divided and includes: a data collection unit (or a data collection processor) 81 configured to collect various data including each modal parameter measured through a modal test on the carbon composite material to be measured, and a data analysis unit (or a data analysis processor) 82 configured to calculate a sensitivity index according to an carbon fiber angle (angle).

In addition, the above-described analysis system 80, as shown in FIG. 8, may be performed including: the output unit 83, which displays measured values collected through the data collection unit 81, various data including the analysis result of the data analysis unit 82, and a processing operation and a state of the analysis system 80 and the like; and the communication unit 84 configured to perform communication in at least one of wired or wireless communication to transmit and receive various data to and from other analysis systems 80 or servers, and a control unit 85 configured to control the overall operation of each unit and analysis system 80.

Here, the data collection unit 81 may be configured to collect measured values by measuring each modal parameter through a modal test on the carbon composite material to be measured, Alternatively, data collected in advance through a modal test may be directly input through a separate input means or configured to transmit through the communication unit 84 by at least one of wired or wireless communication.

In addition, the data analysis unit 82 may be configured to calculate a sensitivity index using only the viscous damping coefficient of the carbon fiber by applying the method for analyzing the damping characteristics of the carbon composite material using the viscous damping coefficient of the carbon fiber as described above with reference to FIGS. 1 to 7 and perform a process of analyzing the damping characteristics.

Furthermore, the above-described output unit 83 may include, for example, a separate display means such as a monitor or a display may be included to perform a process of visually displaying various data and information such as a current state.

In addition, the control unit 85 receives various data and control signals from the central control server to control the overall operation of the analysis system 80, respectively, and at the same time, various data including measurements collected through the data collection unit 81 and sensitivity indices and analysis results calculated through the data analysis unit 82 are stored in separate storage means to build a database on the damping properties of carbon composite material. It may be configured to perform a process of transmitting the constructed data to a central control server, an external device, or another analysis system 80.

Therefore, as described above, each analysis system 80 communicates with each other to exchange various data and is configured to periodically transmit monitoring data to each server at the request from the server or according to a predetermined setting, thereby easily collecting a vast amount of test data.

In addition, the analysis system 80, according to an embodiment of the present disclosure, may further include a user terminal for requesting and receiving data on damping characteristics of the carbon composite material constructed as described above from each analysis system 80 or server.

Here, the user terminal 82, for example, may be configured using a terminal device such as a PC, and preferably, is a personal portable information communication terminal such as a smartphone, tablet PC, or the notebook computer, which may be configured by installing a dedicated application. Still, the present disclosure is not necessarily limited to this configuration, that is, the present disclosure is not necessarily limited to this configuration, and it should be noted by those skilled in the art that the present disclosure may be variously modified and changed as necessary, not departing from the spirit and essence of the present disclosure.

Therefore, according to an embodiment of the present disclosure described above, to provide a method for analyzing damping characteristics of carbon composite material using viscous damping coefficient of carbon fiber and a system for analyzing damping characteristics of carbon composite material using thereof is possible to physically accurately analyze the variation in the damping characteristics of the carbon composite material according to the carbon fiber direction by separating the viscous damping coefficient of carbon fiber that is directly influenced the carbon fiber direction in the modal damping ratio measured data and deriving the sensitivity index. Assuming that the dynamic characteristics of the carbon composite material appear as linear behavior, the damping characteristics of the carbon composite material are expressed as viscous damping coefficient represented by a parallel combination of the viscous damping coefficient of the carbon fiber and the viscous damping coefficient of the binding matrix. The sensitivity index analyzed how the viscous damping coefficient of the carbon composite material changes according to the carbon fiber direction. In this viscous damping coefficient of the carbon composite material, the viscous damping coefficient related to the bonding matrix, which is not changed according to the carbon fiber direction, was eliminated, and the sensitivity index of the carbon composite material was calculated only with the viscous damping coefficient of the carbon fiber. In this way, it was confirmed that the viscous damping coefficient of carbon fiber, which could not be known by the existing analysis method, is proportional to the variation in the resonance frequency (or elastic modulus).

In addition, according to the present disclosure, as described above, the problems of the damping characteristics analysis methods of carbon composite material in the prior art can be solved by providing a damping characteristics analysis method of a carbon composite material and a damping characteristics analysis system of a carbon composite material thereof by using only the viscous damping coefficient of carbon fiber which is configured to analyze the variation in the damping characteristics of the carbon composite material more accurately than the conventional method. Conventionally, a modal damping ratio obtained through a modal test is used to analyze the damping characteristics of carbon composite material, for example, such as CFRP made of carbon fiber. Still, it should be expressed as a viscous damping coefficient under the assumption that it is a linear system. Since this viscous damping coefficient is not dependent only on the modal damping ratio according to the carbon fiber direction and is also influenced by the resonance frequency variation, the variation in the viscous damping coefficient cannot be expressed only by the modal damping ratio. Thus, an error occurred in the sensitivity analysis process because the modal damping ratio includes both the modal characteristics of carbon fiber and binder. To solve these problems described above, the sensitivity index is derived by separating the value of the viscous damping coefficient of the carbon fiber that is influenced directly according to the carbon fiber direction from the measured data of the modal damping ratio.

Through the embodiment of the present disclosure as described above, the method for analyzing the damping characteristics of a carbon composite material using the viscous damping coefficient of the carbon fiber according to the present disclosure and the detailed content of the system for analyzing the damping characteristics of the carbon composite material using the same. However, the present disclosure is not limited only to the contents described in the above-described embodiments. Therefore, the present disclosure may be changed according to design needs and various other factors by those of ordinary skill in the art to which the present disclosure pertains and modifications, changes, combinations, and substitutions are possible.

What is claimed is:

1. A method for analyzing damping characteristics of a carbon composite material using a viscous damping coefficient of the carbon fiber, in which processing for analyzing damping characteristics of a carbon composite material using a viscous damping coefficient of the carbon fiber is performed by a computer or dedicated hardware, the method comprising:
   collecting various data including each modal parameter measured through a modal test for a carbon composite material to be analyzed;
   converting a viscous damping coefficient value of the collected carbon composite material into a mass-normalized equivalent viscous damping coefficient;
   extracting only the viscous damping coefficient for carbon fiber from the converted equivalent viscous damping coefficient;

calculating a sensitivity index according to a direction (angle) of the carbon fiber using the extracted viscous damping coefficient for the carbon fiber; and analyzing the damping characteristics of the carbon composite material based on the calculated sensitivity index, wherein the collecting comprises:

collecting each measured value by measuring the viscous damping coefficient of the carbon composite material at a predetermined reference angle and a predetermined arbitrary angle (θ) through a modal test, or receiving the values of the viscous damping coefficient of the carbon composite material according to a carbon fiber angle measured in advance through a modal test through a separate input means.

2. The method of claim 1, wherein the converting comprises:

performing a process in which the viscous damping coefficient of the carbon composite material for a predetermined reference angle of carbon fiber and a predetermined arbitrary angle (θ) is expressed as an equivalent viscous damping coefficient consisting of a parallel combination of the viscous damping coefficient for carbon fiber and the viscous damping coefficient for the binding matrix by using the following Formula:

$$\frac{1}{\overline{c}_{def,i}} = \frac{1}{\overline{c}_{F0,i}} + \frac{1}{\overline{c}_{M0,i}}$$

$$\frac{1}{\overline{c}_{eq,i}(\theta)} = \frac{1}{\overline{c}_{F,i}(\theta)} + \frac{1}{\overline{c}_{M0,i}}$$

wherein $\overline{C}_{def,i}$, $\overline{C}_{F0,i}$ and $\overline{C}_{M0,i}$ represent the viscous damping coefficients of the carbon composite material, the carbon fiber, and the binding matrix with the carbon fiber angle of 0 degrees in the $i^{th}$ mode, respectively, and wherein $\overline{C}_{eg,i}(\theta)$ and $\overline{C}_{F,i}(\theta)$ represent the viscous damping coefficients of the carbon composite material and the carbon fiber with the carbon fiber angle of θ in the $i^{th}$ mode, respectively.

3. The method of claim 2, further comprising:

merging into a single equation by eliminating the viscosity damping coefficient for the binder matrix from the equivalent viscosity damping coefficient by using the following Formula:

$$\left(1 - \frac{\overline{c}_{F0,i}}{\overline{c}_{F,i}(\theta)}\right) = \overline{c}_{F0,i}\left(\frac{1}{\overline{c}_{def,i}} - \frac{1}{\overline{c}_{eq,i}(\theta)}\right).$$

4. The method of claim 3, wherein the calculating comprises:

calculating the sensitivity index according to the carbon fiber angle (θ) for each mode using the following Formula:

$$I_{F,i}(\theta_k) = \frac{\frac{1}{\overline{c}_{def,i}} - \frac{1}{\overline{c}_{eq,i}(\theta_k)}}{\text{norm}\left\{\sum_{k=1}^{N}\left[\frac{1}{\overline{c}_{def,i}} - \frac{1}{\overline{c}_{eq,i}(\theta_k)}\right]\right\}}.$$

5. The method of claim 4, wherein the analyzing comprises:

analyzing the damping characteristics of the carbon composite material based on the calculated sensitivity index for each mode according to the carbon fiber angle and the variation in the viscous damping coefficient according to the carbon fiber angle.

6. A non-transitory computer-readable recording medium storing instructions to perform a method for analyzing damping characteristics of a carbon composite material using a viscous damping coefficient of the carbon fiber, in which processing for analyzing damping characteristics of a carbon composite material using a viscous damping coefficient of the carbon fiber is performed by a computer or dedicated hardware, the method comprising:

collecting various data including each modal parameter measured through a modal test for a carbon composite material to be analyzed;

converting a viscous damping coefficient value of the collected carbon composite material into a mass-normalized equivalent viscous damping coefficient;

extracting only the viscous damping coefficient for carbon fiber from the converted equivalent viscous damping coefficient;

calculating a sensitivity index according to a direction (angle) of the carbon fiber using the extracted viscous damping coefficient for the carbon fiber; and analyzing the damping characteristics of the carbon composite material based on the calculated sensitivity index, wherein the collecting comprises:

collecting each measured value by measuring the viscous damping coefficient of the carbon composite material at a predetermined reference angle and a predetermined arbitrary angle (θ) through a modal test, or receiving the values of the viscous damping coefficient of the carbon composite material according to a carbon fiber angle measured in advance through a modal test through a separate input means.

7. A damping characteristics analysis system of carbon composite material, the system comprising:

a data collection processor configured to collect various data including each modal parameter measured through a modal test for a carbon composite material to be analyzed;

a coefficient conversion processor configured to covert a viscous damping coefficient value of the collected carbon composite material into a mass-normalized equivalent viscous damping coefficient;

a coefficient extraction processor configured to extract only the viscous damping coefficient for carbon fiber from the converted equivalent viscous damping coefficient;

a sensitivity index calculation processor configured to calculate a sensitivity index according to a direction (angle) of the carbon fiber using the extracted viscous damping coefficient for the carbon fiber;

a damping analysis processor configured to analyze the damping characteristics of the carbon composite material based on the calculated sensitivity index;

an output unit configured to display various data including a collected measurement value and an analysis result of the damping analysis processor, and display various information including a processing operation and status of the analysis system;

a communication unit configured to transmit/receive, via at least one of wired or wireless communication, various data to/from an external device including other analysis systems or servers; and a controller configured to control an overall operation of the analysis system.

8. The system of claim 7, wherein the data collection processor is configured to measure each modal parameter through a modal test for the carbon composite material to be measured and collect measured values, or to directly receive data in advance through a modal test through a separate input means or by at least one of wired or wireless communication through the communication unit.

9. The system of claim 7, wherein the output unit comprises a separate display means including a monitor or a display configured to visually display various data and information, including a current state.

10. The system of claim 7, wherein the controller is configured to control the overall operation of the analysis system, store various data including measured values collected through the data collection processor, the sensitivity index, and analysis result calculated through the data analysis processor in separate storage means to construct a database about the damping characteristics of the carbon composite material, and transmit the constructed data to a server, an external device, or another analysis system.

11. The system of claim 10, further comprising:

a user terminal configured to request and receive desired information to and from each analysis system or server.

12. The system of claim 11, wherein the user terminal is configured to use an information processing terminal device including a PC, or to install a dedicated application on an information and communication terminal portable by an individual, including a smartphone, tablet PC, or laptop.

* * * * *